(12) United States Patent
Nakayama

(10) Patent No.: US 10,420,192 B2
(45) Date of Patent: Sep. 17, 2019

(54) LIGHT SOURCE DEVICE AND ENDOSCOPE SYSTEM

(71) Applicant: OLYMPUS CORPORATION, Tokyo (JP)

(72) Inventor: Noboru Nakayama, Iruma (JP)

(73) Assignee: OLYMPUS CORPORATION, Tokyo (JP)

(*) Notice: Subject to any disclaimer, the term of this patent is extended or adjusted under 35 U.S.C. 154(b) by 95 days.

(21) Appl. No.: 15/687,963

(22) Filed: Aug. 28, 2017

(65) Prior Publication Data

US 2018/0063925 A1 Mar. 1, 2018

(30) Foreign Application Priority Data

Sep. 1, 2016 (JP) .................. 2016-170786

(51) Int. Cl.
*H05B 37/02* (2006.01)
*A61B 1/00* (2006.01)
(Continued)

(52) U.S. Cl.
CPC ..... *H05B 37/0227* (2013.01); *A61B 1/00006* (2013.01); *A61B 1/00009* (2013.01); *A61B 1/00165* (2013.01); *A61B 1/00172* (2013.01); *A61B 1/04* (2013.01); *A61B 1/042* (2013.01); *A61B 1/063* (2013.01); *A61B 1/0669* (2013.01); *A61B 1/07* (2013.01); *H04N 5/2256* (2013.01); *H04N 2005/2255* (2013.01)

(58) Field of Classification Search
CPC .. H05B 37/02; H05B 37/029; H05B 37/0227; A61B 1/00006; A61B 1/00013; A61B 1/07; A61B 1/045; A61B 1/0661; A61B 1/0684; G02B 23/24; G02B 23/26; G02B 23/2484; G02B 23/2469; H04N 5/2256; H04N 2005/2255
See application file for complete search history.

(56) References Cited

U.S. PATENT DOCUMENTS 7,432,970 B2 * 10/2008 Suda .................. H04N 5/23241
348/222.1
9,766,451 B2 * 9/2017 Shimamoto ........ G02B 23/2469
(Continued)

FOREIGN PATENT DOCUMENTS

JP 2008-289711 A 12/2008
JP 5467181 B1 4/2014

*Primary Examiner* — Haissa Philogene
(74) *Attorney, Agent, or Firm* — Scully, Scott, Murphy & Presser, P.C.

(57) ABSTRACT

A light source device includes a light-emitting device configured to emit laser light, a light-receiving device configured to output a received light signal having an output current according to an amount of received laser light, a drive signal supply section configured to supply to the light-emitting device, a drive signal, and a determination section configured to determine occurrence/non-occurrence of a failure in the drive signal supply section based on one of a drive current of the drive signal and a forward voltage of the light-emitting device, and to determine occurrence/non-occurrence of deterioration of the light-emitting device and/or the light-receiving device based on another of the drive current and the forward voltage and the output current.

4 Claims, 5 Drawing Sheets

(51) Int. Cl.
*A61B 1/04* (2006.01)
*A61B 1/06* (2006.01)
*A61B 1/07* (2006.01)
*H04N 5/225* (2006.01)

(56) References Cited

U.S. PATENT DOCUMENTS

| 9,880,380 B2* | 1/2018 | Daidoji .................... A61B 1/04 |
| 10,016,116 B2* | 7/2018 | Tabuchi .................... A61B 1/04 |
| 2016/0220095 A1* | 8/2016 | Shimomura ....... A61B 1/00006 |
| 2019/0117041 A1* | 4/2019 | Tanaka ..................... A61B 1/00 |

* cited by examiner

LIGHT SOURCE DEVICE AND ENDOSCOPE SYSTEM

CROSS REFERENCE TO RELATED APPLICATION

This application claims the benefit of Japanese Application No. 2016-170786 filed in Japan on Sep. 1, 2016, the contents of which are incorporated herein by this reference.

BACKGROUND OF THE INVENTION

1. Field of the Invention

The present invention relates to a light source device and an endoscope system which are used for observation of an object existing inside a body cavity of a living body.

2. Description of the Related Art

With regard to endoscopic observation in a medical field, configurations according to which an object existing inside a body cavity of a living body is illuminated by using light emitted from a light-emitting device such as a laser diode (LD) or a light-emitting diode (LED) have been proposed in recent years.

More specifically, for example, Japanese Patent No. 5467181 discloses a configuration of an endoscope system including a light source device provided with LEDs of three colors, red, green and blue, according to which whether a failure has occurred in each of the LEDs of three colors is determined. Japanese Patent No. 5467181 also discloses a configuration according to which, in a case where a failure has occurred in an LED of one color among the LEDs of three colors, red, green and blue, LEDs of two colors other than the LED of the one color are caused to emit light, and image processing corresponding to the two LEDs is performed.

On the other hand, for example, Japanese Patent Application Laid-Open Publication No. 2008-289711 discloses a configuration of an endoscope apparatus including an apparatus main body section provided with a laser diode and a light source drive section, according to which, in a case where an abnormality is recognized in a current value of a current supplied to the laser diode by the light source drive section, radiation of laser light from the laser diode is stopped.

SUMMARY OF THE INVENTION

A light source device according to an aspect of the present invention includes a light-emitting device configured to emit laser light, a light-receiving device configured to receive a part of the laser light emitted from the light-emitting device, and to generate, and output, a received light signal having an output current of a magnitude according to an amount of the received laser light, a drive signal supply section configured to generate, and supply to the light-emitting device, a drive signal for driving the light-emitting device, and a determination section configured to determine occurrence/non-occurrence of a failure in the drive signal supply section based on a first detected amount that is obtained by detecting one of a magnitude of a drive current of the drive signal and a magnitude of a forward voltage of the light-emitting device and to acquire a determination result, and to determine occurrence/non-occurrence of deterioration of the light-emitting device and/or the light-receiving device based on a second detected amount that is obtained by detecting another of the magnitude of the drive current and the magnitude of the forward voltage and a third detected amount that is obtained by detecting a magnitude of the output current and to acquire a determination result.

An endoscope system according to an aspect of the present invention includes a light source device including a light-emitting device configured to emit laser light, a light-receiving device configured to receive a part of the laser light emitted from the light-emitting device, and to generate, and output, a received light signal having an output current of a magnitude according to an amount of the received laser light, a drive signal supply section configured to generate, and supply to the light-emitting device, a drive signal for driving the light-emitting device, and a determination section configured to determine occurrence/non-occurrence of a failure in the drive signal supply section based on a first detected amount that is obtained by detecting one of a magnitude of a drive current of the drive signal and a magnitude of a forward voltage of the light-emitting device and to acquire a determination result, and to determine occurrence/non-occurrence of deterioration of the light-emitting device and/or the light-receiving device based on a second detected amount that is obtained by detecting another of the magnitude of the drive current and the magnitude of the forward voltage and a third detected amount that is obtained by detecting a magnitude of the output current and to acquire a determination result, an optical fiber configured to transmit laser light emitted from the light-emitting device, an actuator section configured to be able to displace a radiation position of laser light that is emitted onto an object through the optical fiber, by swinging an emitting end portion of the optical fiber, a light detection section configured to detect return light from the object, and to generate, and sequentially output, a signal according to the detected return light, and an image processing section configured to generate an observation image of the object based on a signal that is sequentially outputted from the light detection section.

DETAILED DESCRIPTION OF THE PREFERRED EMBODIMENT(S)

Hereinafter, an embodiment of the present invention will be described with reference to the drawings.

FIGS. 1 to 7 are related to the embodiment of the present invention.

Figure 1:
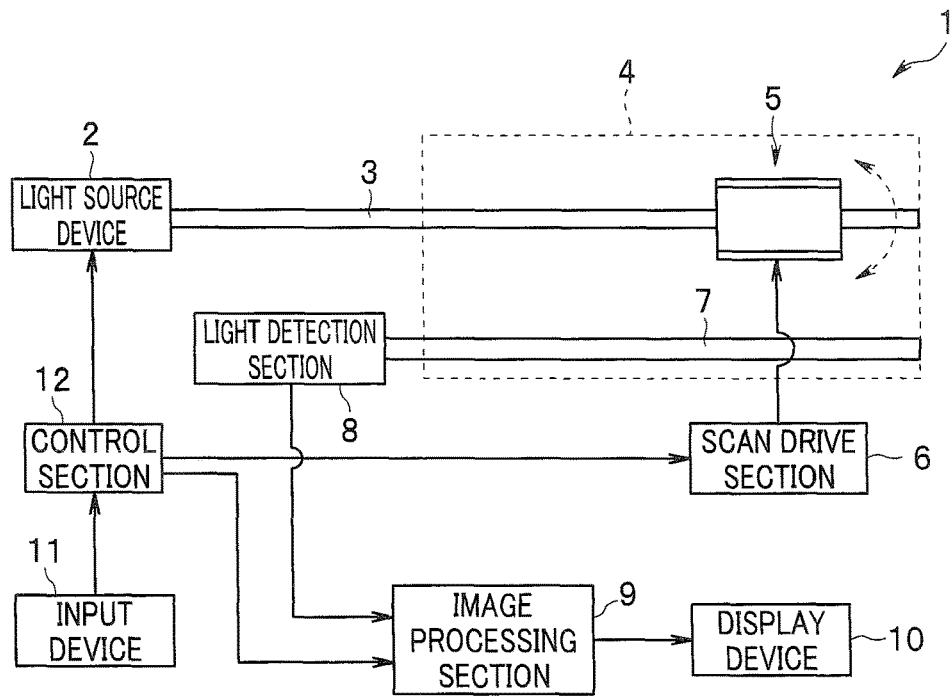
FIG. 1 is a diagram showing a configuration of main parts of an endoscope system including a light source device according to an embodiment.

For example, as shown in FIG. 1, an endoscope system 1 includes a light source device 2, an optical fiber 3, a scanning endoscope (hereinafter abbreviated as endoscope) 4, an actuator section 5, a scan drive section 6, an optical fiber bundle 7, a light detection section 8, an image processing section 9, a display device 10, an input device 11, and a control section 12.

The light source device 2 is configured to be able to generate illumination light for illuminating an object, and to supply the illumination light to an incident end portion of the optical fiber 3. Also, the light source device 2 is configured to be able to supply light of one color among R light, which is red laser light, G light, which is green laser light, and B light, which is blue laser light, as the illumination light, to the incident end portion of the optical fiber 3, under the control by the control section 12. Note that a specific configuration of the light source device 2 will be described below.

For example, the optical fiber 3 is a single-mode fiber. The incident end portion, of the optical fiber 3, including a light incident surface is connected to the light source device 2. Also, an emitting end portion, of the optical fiber 3, including a light emitting surface is arranged at a distal end portion of the endoscope 4. That is, the optical fiber 3 is configured to be able to transmit illumination light (laser light) supplied from the light source device 2, and to emit the illumination light onto an object from the emitting end portion.

The endoscope 4 has an elongated shape that can be inserted into a body cavity of a subject, and is configured to be able to scan an object inside the body cavity by the illumination light supplied from the light source device 2.

The optical fiber 3 and the optical fiber bundle 7 are each inserted inside the endoscope 4. Also, the actuator section 5 which is configured to swing the emitting end portion of the optical fiber 3 according to a drive signal supplied from the scan drive section 6 is provided inside the endoscope 4.

Figure 2:
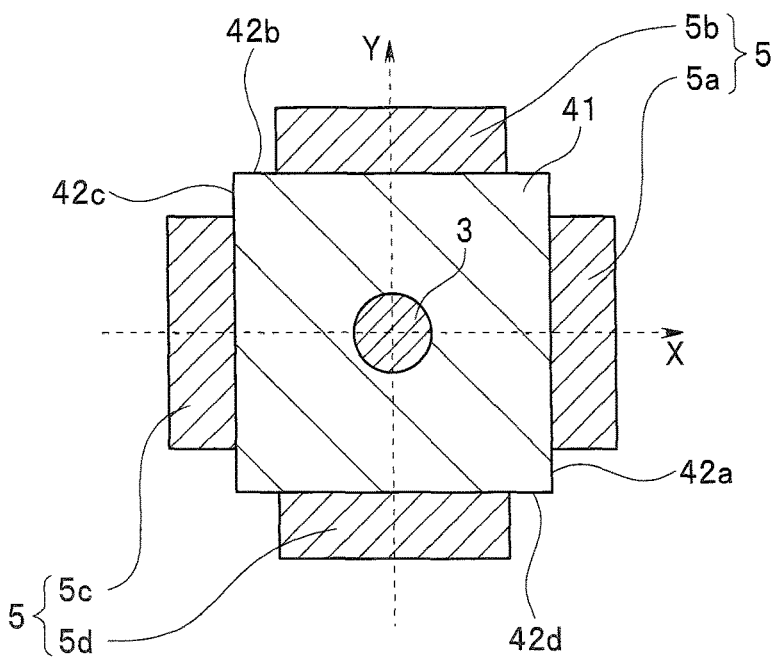
FIG. 2 is a cross-sectional diagram for describing an example of a configuration of an actuator section.

For example, the optical fiber 3 and the actuator section 5 are arranged in a positional relationship as shown in FIG. 2 at a cross-section perpendicular to a longitudinal axis direction of the endoscope 4. FIG. 2 is a cross-sectional diagram for describing an example of a configuration of the actuator section.

As shown in FIG. 2, between the optical fiber 3 and the actuator section 5, the emitting end portion of the optical fiber 3 is arranged in a penetrating manner, and also, a ferrule 41, as a joining member, having the actuator section 5 disposed on each outer surface is arranged. More specifically, the ferrule 41 is formed of zirconia (ceramics) or nickel, for example.

As shown in FIG. 2, the ferrule 41 is formed as a quadrangular prism which is formed in such a manner that a cross-section which is perpendicular to the longitudinal axis direction of the endoscope 4 is a square with a center axis of the optical fiber 3 at the center, and includes side surfaces 42a and 42c that are perpendicular to an X-axis direction, which is a first axis direction orthogonal to the longitudinal axis direction, and side surfaces 42b and 42d that are perpendicular to a Y-axis direction, which is a second axis direction orthogonal to the longitudinal axis direction. Note that the ferrule 41 may be formed to have a shape other than the quadrangular prism as long as the ferrule 41 has a columnar shape.

The actuator section 5 is configured to be able to displace, along a predetermined scan path, the radiation position of illumination light (laser light) emitted onto an object through the emitting end portion of the optical fiber 3, by swinging the emitting end portion based on a drive signal that is supplied from the scan drive section 6. Moreover, as shown in FIG. 2, the actuator section 5 includes a piezoelectric element 5a, which is arranged along the side surface 42a, a piezoelectric element 5b, which is arranged along the side surface 42b, a piezoelectric element 5c, which is arranged along the side surface 42c, and a piezoelectric element 5d, which is arranged along the side surface 42d.

The piezoelectric element 5a-5d has a polarization direction which is individually set in advance, and is configured to expand or contract according to a drive signal that is supplied from the scan drive section 6.

For example, the scan drive section 6 includes a drive circuit. Also, the scan drive section 6 is configured to generate a drive signal for driving the actuator section 5, under the control by the control section 12, and to supply the generated drive signal to the actuator section 5.

For example, the optical fiber bundle 7 is configured by bundling a plurality of optical fibers. An incident end portion of the optical fiber bundle 7 is arranged at the distal end portion of the endoscope 4. Also, an emitting end portion, of the optical fiber bundle 7, including a light emitting surface is connected to the light detection section 8. That is, the optical fiber bundle 7 is configured to be able to receive return light (reflected light) from an object at the distal end portion of the endoscope 4, and to transmit the received return light to the light detection section 8.

For example, the light detection section 8 includes a light detection element and an A/D converter. Also, the light detection section 8 is configured to detect return light entering through the emitting end portion of the optical fiber bundle 7, to generate an electrical signal according to the amount of the detected return light, and to convert the generated electrical signal into a digital signal and to successively output the signal.

For example, the image processing section 9 includes an image processing circuit. Also, the image processing section 9 is configured to perform a mapping process of mapping, as pixel information, a brightness value according to a digital signal that is outputted from the light detection section 8 during scanning of an object along one of a first spiral scan path (described below) and a second spiral scan path (described below), for example, to thereby generate an observation image of the object, and to output the generated observation image to the display device 10.

For example, the display device 10 includes a liquid crystal display. Also, the display device 10 is configured to be able to display an observation image that is outputted from the image processing section 9, and the like.

For example, the input device 11 includes a user interface that can be operated by a user, such as a switch and/or a button. Also, the input device 11 is configured to be able to issue, to the control section 12, various instructions according to operations of a user.

For example, the control section 12 includes an integrated circuit including an arithmetic circuit and a control circuit, and is configured to control each of the light source device 2, the scan drive section 6, and the image processing section 9.

For example, the control section 12 is configured to perform control so as to scan an object along a spiral scan path while radiating the R light, the G light, and the B light on the object in a time-division manner.

Figure 3:
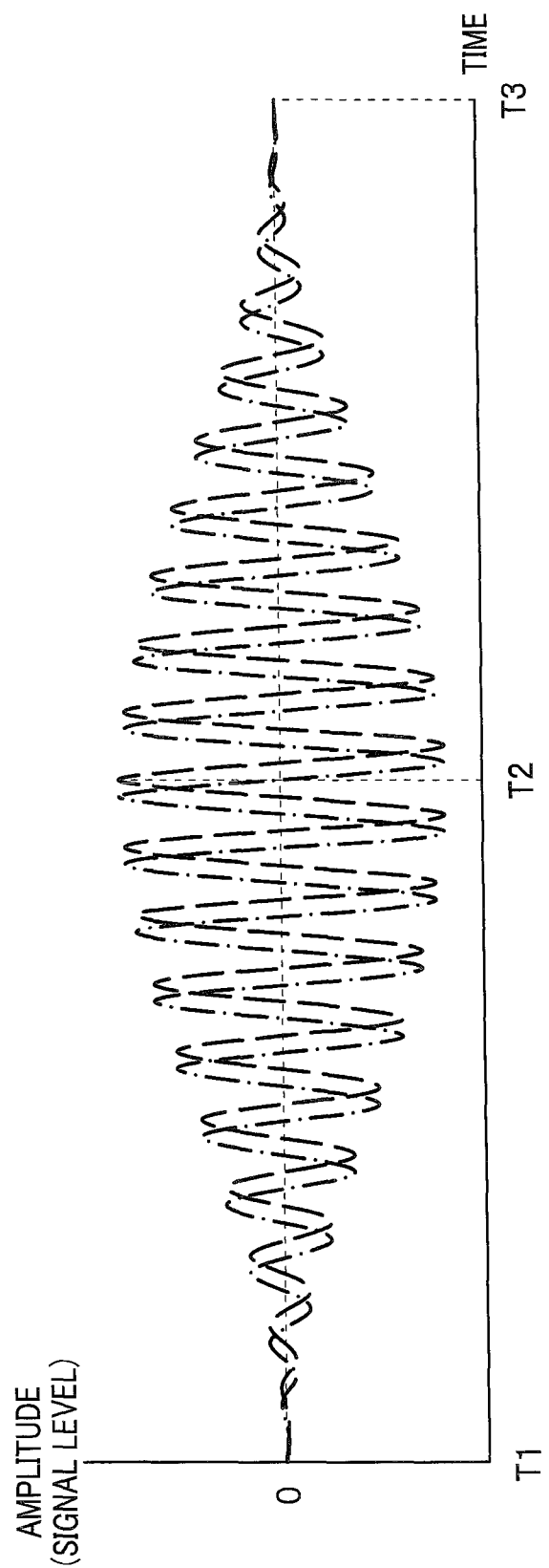
FIG. 3 is a diagram showing respective examples of signal waveforms of drive signals that are supplied to the actuator section.

More specifically, for example, the control section 12 controls the scan drive section 6 such that a drive signal DSX having a first signal waveform as shown by a broken line in FIG. 3 and a drive signal DSY having a second signal waveform as shown by a dashed-dotted line in FIG. 3 are generated, and also, controls the light source device 2 such that the R light, the G light, and the B light are repeatedly supplied in the order to the optical fiber 3. Furthermore, the scan drive section 6 supplies the drive signal DSX generated under the control by the control section 12 to the piezoelectric elements 5a and 5c of the actuator section 5, and supplies the drive signal DSY generated under the control by the control section 12 to the piezoelectric elements 5b and 5d of the actuator section 5. Note that the first signal waveform shown by the broken line in FIG. 3 is a waveform that is obtained by applying predetermined modulation on a sine wave, for example. Also, the second signal waveform shown by the dashed-dotted line in FIG. 3 is a waveform obtained by shifting the phase of the first signal waveform by 90 degrees. FIG. 3 is a diagram showing respective examples of the signal waveforms of the drive signals that are supplied to the actuator section.

Figure 4:
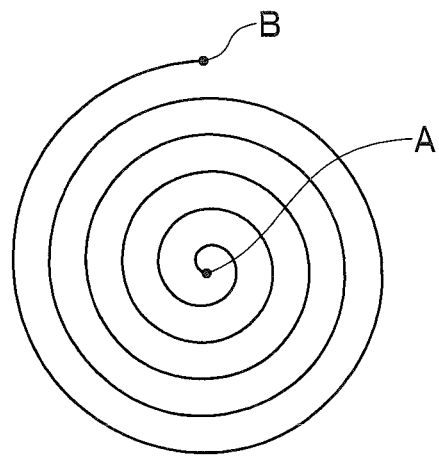
FIG. 4 is a diagram for describing displacement over time of a radiation position of illumination light from a center point A to an outermost point B.
Figure 5:
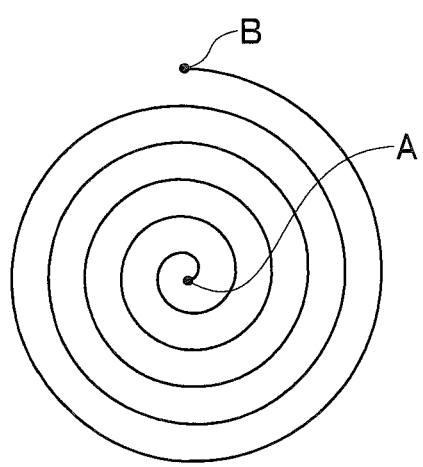
FIG. 5 is a diagram for describing displacement over time of the radiation position of illumination light from the outermost point B to the center point A.

Due to the control and the operation as described above, the emitting end portion of the optical fiber 3 is swung in a spiral manner, and the surface of an object is scanned along a spiral scan path as shown in FIGS. 4 and 5. FIG. 4 is a diagram for describing displacement over time of a radiation position of illumination light from a center point A to an outermost point B. FIG. 5 is a diagram for describing displacement over time of the radiation position of illumination light from the outermost point B to the center point A.

More specifically, first, at a time T1, illumination light is radiated on a position, on a surface of an object, corresponding to the center point A of the radiation position of the illumination light. Then, as the amplitude (signal levels) of the drive signals DSX and DSY is increased from the time T1 to a time T2, the radiation position of the illumination light on the surface of the object is displaced along the first spiral scan path extending from the center point A toward the outside, and when the time T2 is reached, the illumination light is radiated on the outermost point B of the radiation position of the illumination light on the surface of the object. Then, as the amplitude (signal levels) of the drive signals DSX and DSY is reduced from the time T2 to a time T3, the radiation position of the illumination light on the surface of the object is displaced along the second spiral scan path extending from the outermost point B toward the inside, and when the time T3 is reached, the illumination light is radiated on the center point A on the surface of the object.

For example, the control section 12 is configured to control the image processing section 9 such that an image for one frame is generated by using digital signals that are outputted from the light detection section 8 while the object is being scanned along one scan path of the first spiral scan path and the second spiral scan path, and such that generation of an image using digital signals that are outputted from the light detection section 8 is not performed while the object is being scanned along the other scan path different from the one scan path.

Figure 6:
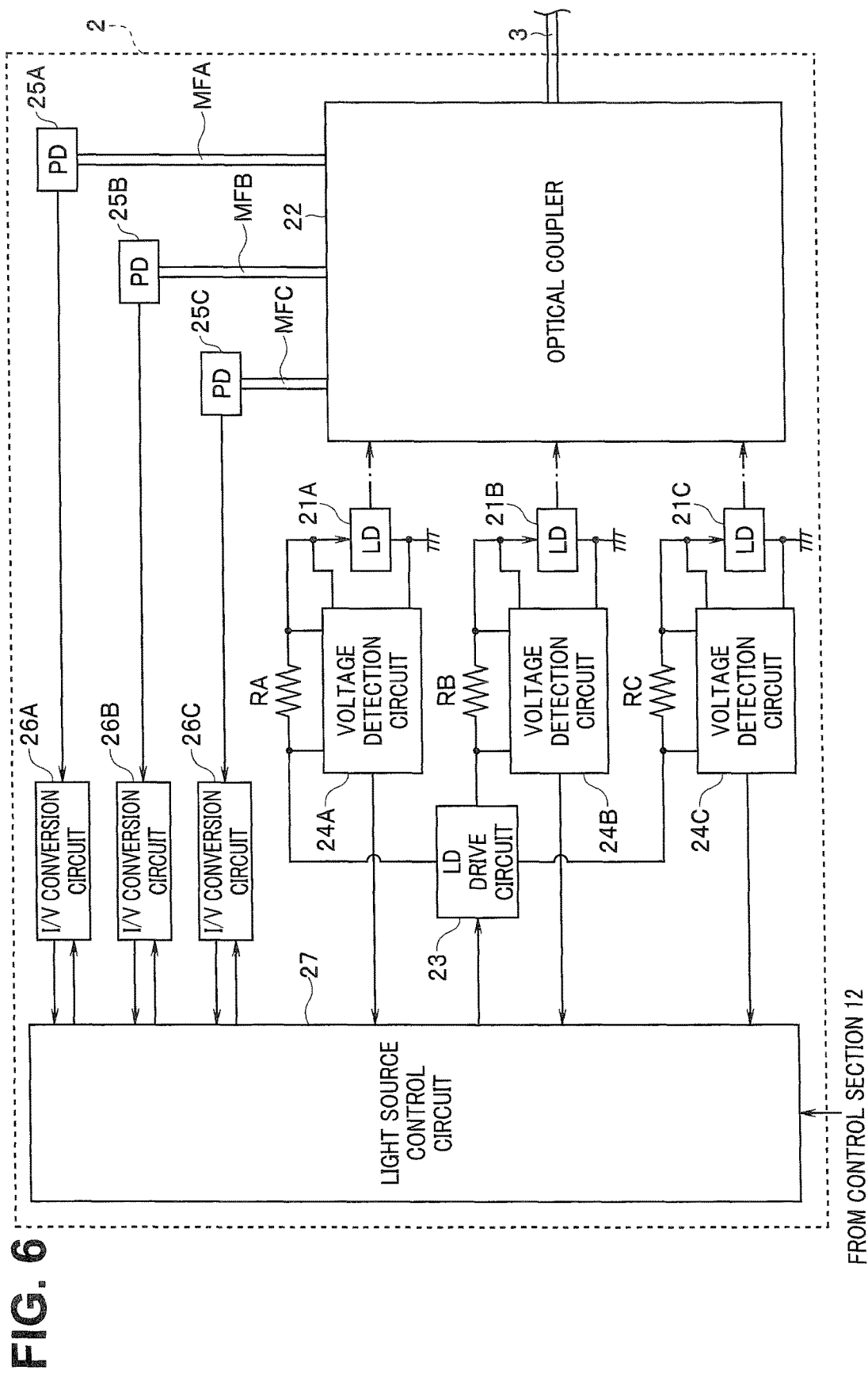
FIG. 6 is a diagram showing an example of a specific configuration of the light source device according to the embodiment.

Now, an example of a specific configuration of the light source device 2 will be described with reference to FIG. 6. FIG. 6 is a diagram showing an example of a specific configuration of the light source device according to the embodiment.

For example, as shown in FIG. 6, the light source device 2 includes LDs (laser diodes) 21A-21C, an optical coupler 22, an LD drive circuit 23, voltage detection circuits 24A-24C, PDs (photodiodes) 25A-25C, I/V (current/voltage) conversion circuits 26A-26C, and a light source control circuit 27.

The LD 21A is configured as a light-emitting device that is driven according to an LD drive signal supplied from the LD drive circuit 23. Also, the LD 21A is configured to generate R light of the amount according to the LD drive signal supplied from the LD drive circuit 23.

The LD 21B is configured as a light-emitting device that is driven according to an LD drive signal supplied from the LD drive circuit 23. Also, the LD 21B is configured to generate G light of the amount according to the LD drive signal supplied from the LD drive circuit 23.

The LD 21C is configured as a light-emitting device that is driven according to an LD drive signal supplied from the LD drive circuit 23. Also, the LD 21C is configured to generate B light of the amount according to the LD drive signal supplied from the LD drive circuit 23.

The optical coupler 22 is configured to be able to cause a part of R light emitted from the LD 21A to enter an optical fiber MFA for monitoring, while emitting the R light to the optical fiber 3. Also, the optical coupler 22 is configured to be able to cause a part of G light emitted from the LD 21B to enter an optical fiber MFB for monitoring, while emitting the G light to the optical fiber 3. Moreover, the optical coupler 22 is configured to be able to cause a part of B light emitted from the LD 21C to enter an optical fiber MFC for monitoring, while emitting the B light to the optical fiber 3.

The LD drive circuit 23 has a function of a drive signal supply section, and is configured to generate LD drive signals for driving the LDs 21A, 21B and 21C under the control by the light source control circuit 27. Also, the LD drive circuit 23 is configured to separately supply the LD drive signals generated in the above manner to the LDs 21A, 21B and 21C.

The voltage detection circuit 24A is configured to detect a potential difference between both ends of a resistor RA provided between the LD 21A and the LD drive circuit 23, that is, a drive voltage VDA, which is the voltage of an LD drive signal that is supplied from the LD drive circuit 23 to the LD 21A, and to generate, and output to the light source control circuit 27, a signal indicating the detected drive voltage VDA. Also, the voltage detection circuit 24A is configured to detect a potential difference between both ends of the LD 21A, that is, a forward voltage VFA, which is a voltage that changes according to the amount of light emission of the LD 21A, and to generate, and output to the light source control circuit 27, a signal indicating the detected forward voltage VFA.

The voltage detection circuit 24B is configured to detect a potential difference between both ends of a resistor RB provided between the LD 21B and the LD drive circuit 23, that is, a drive voltage VDB, which is a voltage of an LD drive signal that is supplied from the LD drive circuit 23 to the LD 21B, and to generate, and output to the light source control circuit 27, a signal indicating the detected drive voltage VDB. Also, the voltage detection circuit 24B is configured to detect a potential difference between both ends of the LD 21B, that is, a forward voltage VFB, which is a voltage that changes according to the amount of light emission of the LD 21B, and to generate, and output to the light source control circuit 27, a signal indicating the detected forward voltage VFB.

The voltage detection circuit 24C is configured to detect a potential difference between both ends of a resistor RC provided between the LD 21C and the LD drive circuit 23, that is, a drive voltage VDC, which is a voltage of an LD drive signal that is supplied from the LD drive circuit 23 to the LD 21C, and to generate, and output to the light source control circuit 27, a signal indicating the detected drive voltage VDC. Also, the voltage detection circuit 24C is configured to detect a potential difference between both ends of the LD 21C, that is, a forward voltage VFC, which is a voltage that changes according to the amount of light emission of the LD 21C, and to generate, and output to the light source control circuit 27, a signal indicating the detected forward voltage VFC.

The PD 25A is configured as a light-receiving device that receives R light emitted through the optical fiber MFA, and that generates, and outputs to the I/V conversion circuit 26A, a received light signal having an output current IPA, which is a current of a magnitude according to the amount of received R light. That is, the PD 25A is configured to receive a part of R light emitted from the LD 21A, and to generate, and output to the I/V conversion circuit 26A, a received light signal having the output current IPA of a magnitude according to the amount of the received R light.

The PD 25B is configured as a light-receiving device that receives G light emitted through the optical fiber MFB, and that generates, and outputs to the I/V conversion circuit 26B, a received light signal having an output current IPB, which is a current of a magnitude according to the amount of received G light. That is, the PD 25B is configured to receive a part of G light emitted from the LD 21B, and to generate, and output to the I/V conversion circuit 26B, a received light signal having the output current IPB of a magnitude according to the amount of the received G light.

The PD 25C is configured as a light-receiving device that receives B light emitted through the optical fiber MFC, and that generates, and outputs to the I/V conversion circuit 26C, a received light signal having an output current IPC, which is a current of a magnitude according to the amount of received B light. That is, the PD 25C is configured to receive a part of B light emitted from the LD 21C, and to generate, and output to the I/V conversion circuit 26C, a received light signal having the output current IPC of a magnitude according to the amount of the received B light.

The I/V conversion circuit 26A is configured to convert the output current IPA of the received light signal outputted from the PD 25A into an output voltage VPA, and to generate, and output to the light source control circuit 27, a signal indicating the output voltage VPA obtained by the conversion. Also, the I/V conversion circuit 26A is configured to set, under the control by the light source control circuit 27, an I/V conversion factor MPA that is used at the time of conversion of the output current IPA into the output voltage VPA.

The I/V conversion circuit 26B is configured to convert the output current IPB of the received light signal outputted from the PD 25B into an output voltage VPB, and to generate, and output to the light source control circuit 27, a signal indicating the output voltage VPB obtained by the conversion. Also, the I/V conversion circuit 26B is configured to set, under the control by the light source control circuit 27, an UV conversion factor MPB that is used at the time of conversion of the output current IPB into the output voltage VPB.

The I/V conversion circuit 26C is configured to convert the output current IPC of the received light signal outputted from the PD 25C into an output voltage VPC, and to generate, and output to the light source control circuit 27, a signal indicating the output voltage VPC obtained by the conversion. Also, the I/V conversion circuit 26C is configured to set, under the control by the light source control circuit 27, an I/V conversion factor MPC that is used at the time of conversion of the output current IPC into the output voltage VPC.

The light source control circuit 27 is configured to be able to control to cause the LDs 21A, 21B and 21C to individually emit light or to stop emitting light, under the control by the control section 12. Also, the light source control circuit 27 has functions of a determination section and a light source control section.

The light source control circuit 27 is configured to monitor, based on signals outputted from the voltage detection circuit 24A and the I/V conversion circuit 26A, each of a drive current IDA, which is a current of a magnitude according to the drive voltage VDA, the forward voltage VFA, and the output current IPA, which is a current of a magnitude according to the output voltage VPA. The light source control circuit 27 is also configured to determine, based on the magnitude of the drive current IDA, the magnitude of the forward voltage VFA, and the magnitude of the output current IPA, occurrence/non-occurrence of a failure in the LD drive circuit 23, occurrence/non-occurrence of deterioration of the LD 21A, and occurrence/non-occurrence of deterioration of the PD 25A, and to acquire determination results. Furthermore, the light source control circuit 27 is configured to control the LD drive circuit 23 and/or the I/V conversion circuit 26A according to a determination result acquired in the above manner.

The light source control circuit 27 is configured to monitor, based on signals outputted from the voltage detection circuit 24B and the I/V conversion circuit 26B, each of a drive current IDB, which is a current of a magnitude according to the drive voltage VDB, the forward voltage VFB, and the output current IPB, which is a current of a magnitude according to the output voltage VPB. The light source control circuit 27 is also configured to determine, based on the magnitude of the drive current IDB, the magnitude of the forward voltage VFB, and the magnitude of the output current IPB, occurrence/non-occurrence of a failure in the LD drive circuit 23, occurrence/non-occurrence of deterioration of the LD 21B, and occurrence/non-occurrence of deterioration of the PD 25B, and to acquire determination results. Furthermore, the light source control circuit 27 is configured to control the LD drive circuit 23 and/or the I/V conversion circuit 26B according to the determination result acquired in the above manner.

The light source control circuit 27 is configured to monitor, based on signals outputted from the voltage detection circuit 24C and the I/V conversion circuit 26C, each of a drive current IDC, which is a current of a magnitude according to the drive voltage VDC, the forward voltage VFC, and the output current IPC, which is a current of a magnitude according to the output voltage VPC. The light source control circuit 27 is also configured to determine, based on the magnitude of the drive current IDC, the magnitude of the forward voltage VFC, and the magnitude of the output current IPC, occurrence/non-occurrence of a failure in the LD drive circuit 23, occurrence/non-occurrence of deterioration of the LD 21C, and occurrence/non-occurrence of deterioration of the PD 25C, and to acquire determination results. Furthermore, the light source control circuit 27 is configured to control the LD drive circuit 23 and/or the I/V conversion circuit 26C according to the determination result acquired in the above manner.

Next, an effect of the present embodiment will be described. Note that, in the following, for the sake of simplicity, a specific example of an operation performed at the light source device 2 will be mainly described, and description of various types of operations performed at respective sections other than the light source device 2 will be omitted as appropriate.

A user, such as a surgeon, connects each section of the endoscope system 1 and turns on the power, and then, presses a scan start switch (not shown) of the input device 11, for example, to thereby instruct the control section 12 to start scanning of an object by the endoscope 4.

When pressing of the scan start switch of the input device 11 is detected, the control section 12 controls the light source device 2 such that the R light, the G light, and the B light are radiated on the object in a time-division manner, for example. Also, when pressing of the scan start switch of the input device 11 is detected, the control section 12 controls the scan drive section 6 such that the object is scanned along the first and the second spiral scan path as shown in FIG. 4 or 5, for example. Moreover, when pressing of the scan start switch of the input device 11 is detected, the control section 12 controls the image processing section 9 such that an image for one frame is generated by using digital signals that are outputted from the light detection section 8 while the object is being scanned along the first spiral scan path, and such that generation of an image using digital signals that are outputted from the light detection section 8 is not performed while the object is being scanned along the second scan path, for example. According to the control by the control section 12 as described above, an observation image that is obtained by scanning an object along the first spiral scan path is displayed by the display device 10.

The light source control circuit 27 controls the LD drive circuit 23 such that the LDs 21A, 21B and 21C are repeatedly caused to emit light in the order, under the control by the control section 12 as described above. Moreover, while performing control as described above, the light source control circuit 27 also determines occurrence/non-occurrence of a failure in the LD drive circuit 23, occurrence/non-occurrence of deterioration of the LDs 21A-21C, and occurrence/non-occurrence of deterioration of the PDs 25A-25C and acquires determination results, and performs control according to the acquired determination results.

Figure 7:
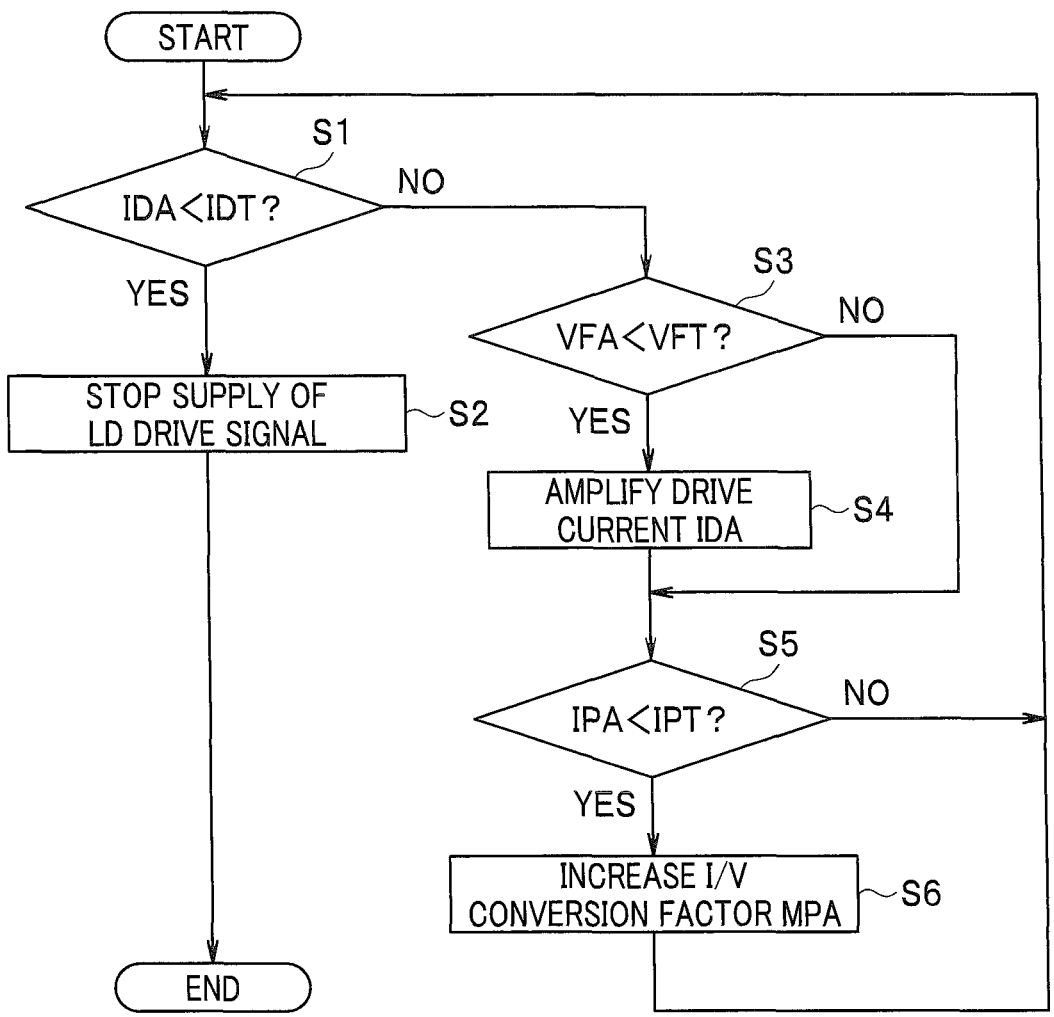
FIG. 7 is a flowchart for describing a specific example of an operation that is performed by a light source control circuit of the light source device according to the embodiment.

A specific example of an operation that is performed at the light source control circuit 27 will now be described with reference to FIG. 7. Note that, in the following, an example is described for a case where the light source control circuit 27 controls the LD drive circuit 23 so as to set an initial value of the drive current IDA as a reference drive current IDT, and also, determines occurrence/non-occurrence of a failure in the LD drive circuit 23, occurrence/non-occurrence of deterioration of the LD 21A, and occurrence/non-occurrence of deterioration of the PD 25A. Moreover, in the following, description is given assuming that the temperature of the LD 21A is constant or substantially constant. Moreover, the reference drive current IDT is assumed to be a drive current of a known magnitude that is necessary for generation of R light of a predetermined amount ALR by the LD 21A. FIG. 7 is a flowchart for describing a specific example of an operation that is performed by the light source control circuit of the light source device according to the embodiment.

The light source control circuit 27 detects the drive current IDA based on the drive voltage VDA that is indicated by a signal outputted from the voltage detection circuit 24A, and also, determines whether the magnitude of the detected drive current IDA is smaller than the magnitude of the reference drive current IDT (FIG. 7, step S1). In other words, in step S1 in FIG. 7, the light source control circuit 27 performs an operation of detecting the drive current IDA based on the drive voltage VDA that is indicated by a signal outputted from the voltage detection circuit 24A, and also, of determining whether the detected drive current IDA is reduced from the reference drive current IDT. In further other words, in step S1 in FIG. 7, the light source control circuit 27 performs an operation of determining occurrence/non-occurrence of a failure in the LD drive circuit 23 based on the detected amount obtained by detecting the drive current IDA, and of acquiring a determination result.

In the case where the magnitude of the drive current IDA is detected to be smaller than the magnitude of the reference drive current IDT (S1: YES), that is, in the case where the drive current IDA is detected to have been reduced from the reference drive current IDT, the light source control circuit 27 acquires a determination result indicates occurrence of a failure in the LD drive circuit 23. Then, the light source control circuit 27 controls the LD drive circuit 23 so as to stop supply of LD drive signals to the LD 21A, according to the determination result that indicates occurrence of a failure in the LD drive circuit 23 (FIG. 7, step S2).

In the case where the magnitude of the drive current IDA is detected to be equal to or larger than the magnitude of the reference drive current IDT (S1: NO), that is, in the case where the drive current IDA is detected as not reduced from the reference drive current IDT, the light source control circuit 27 acquires a determination result that indicates non-occurrence of a failure in the LD drive circuit 23, and then, subsequently performs the operation in step S3 in FIG. 7, described below.

The light source control circuit 27 determines whether the magnitude of the forward voltage VFA that is indicated by a signal outputted from the voltage detection circuit 24A is smaller than the magnitude of a reference forward voltage VFT (FIG. 7, step S3). In other words, in step S3 in FIG. 7, the light source control circuit 27 determines whether the forward voltage VFA that is indicated by a signal outputted from the voltage detection circuit 24A is reduced from the reference forward voltage VFT. Note that the reference forward voltage VFT is a forward voltage of a known magnitude that is detected when an LD drive signal (of the reference drive current IDT) for generating R light of a predetermined amount ALR is supplied to the LD 21A, for example.

In the case where the magnitude of the forward voltage VFA is detected to be smaller than the magnitude of the reference forward voltage VFT (S3: YES), that is, in the case where the forward voltage VFA is detected to have been reduced from the reference forward voltage VFT, the light source control circuit 27 acquires a determination result that indicates occurrence of deterioration of the LD 21A. Then, according to the determination result that indicates occurrence of deterioration of the LD 21A, the light source control circuit 27 controls the LD drive circuit 23 so as to amplify the drive current IDA of the LD drive signal that is supplied to the LD 21A, that is, so as to increase the detected amount that is obtained by detecting the forward voltage VFA (FIG. 7, step S4), and then, subsequently performs the operation in step S5 in FIG. 7. Note that a value that is greater than one and that can cause the forward voltage VFA immediately before performance of the operation in step S4 in FIG. 7 to coincide with the reference forward voltage VFT is acquired as an amplification factor that is used for amplification of the drive current IDA, for example. Also, the amplification factor that is used for amplification of the drive current IDA is acquired based on current-voltage characteristics of the LD 21A and the magnitude of the drive current IDA immediately before performance of the operation in step S4 in FIG. 7, for example.

In the case where the magnitude of the forward voltage VFA is detected to be equal to or larger than the magnitude of the reference forward voltage VFT (S3: NO), that is, in the case where the forward voltage VFA is detected as not reduced from the reference forward voltage VFT, the light source control circuit 27 acquires a determination result that indicates non-occurrence of deterioration of the LD 21A, and then, subsequently performs the operation in step S5 in FIG. 7, described below. That is, in the case where the operation in step S4 in FIG. 7 is not performed, the amplification factor that is used for amplification of the drive current IDA is maintained.

The light source control circuit 27 detects the output current IPA based on the output voltage VPA that is indicated by a signal outputted from the I/V conversion circuit 26A, and also, determines whether the magnitude of the detected output current IPA is smaller than a reference output current IPT (FIG. 7, step S5). In other words, in step S5 in FIG. 7, the light source control circuit 27 detects the output current IPA based on the output voltage VPA that is indicated by a signal outputted from the I/V conversion circuit 26A, and also, determines whether the detected output current IPA is reduced from the reference output current IPT. Note that the reference output current IPT is an output current of a known magnitude according to the amount of R light that is received at the PD 25A at the time of emission of R light of the predetermined amount ALR from the LD 21A, for example.

In the case where the magnitude of the output current IPA is detected to be smaller than the magnitude of the reference output current IPT (S5: YES), that is, in the case where the output current IPA is detected to have been reduced from the reference output current IPT, the light source control circuit 27 acquires a determination result that indicates occurrence of deterioration of the PD 25A. Then, according to the determination result that indicates occurrence of deterioration of the PD 25A, the light source control circuit 27 controls the I/V conversion circuit 26A so as to increase the conversion factor MPA at the time of conversion of the output current IPA into the output voltage VPA to a factor greater than one, that is, so as to increase the detected amount that is obtained by detecting the output current IPA (FIG. 7, step 6), and then, performs again the operation in step S1 in FIG. 7, described above.

More specifically, for example, in the case where the LD drive signal of the reference drive current IDT is supplied to the LD 21A, if the magnitude of the output current IPA is detected to be 0.5 times the reference output current IPT, the light source control circuit 27 controls the I/V conversion circuit 26A so as to double the conversion factor MPA. That is, a value that is greater than one and that can cause the output current IPA immediately before performance of the operation in step S6 in FIG. 7 to coincide with the reference output current IPT is acquired as the conversion factor MPA that is set according to the operation in step S6 in FIG. 7, for example.

In the case where the magnitude of the output current IPA is detected to be equal to or larger than the magnitude of the reference output current IPT (S5: NO), that is, in the case where the output current IPA is detected as not reduced from the reference output current IPT, the light source control circuit 27 acquires a determination result that indicates non-occurrence of deterioration of the PD 25A, and then, performs again the operation in step S1 in FIG. 7, described above. That is, in the case where the operation in step S6 in FIG. 7 is not performed, the conversion factor MPA at the I/V conversion circuit 26A is maintained.

As described above, the light source control circuit 27 performs, in steps S3 and S5 in FIG. 7, an operation of determining occurrence/non-occurrence of deterioration of the LD 21A and/or the PD 25A based on the detected amount that is obtained by detecting the magnitude of the forward voltage VFA and the detected amount that is obtained by detecting the magnitude of the output current IPA, and of acquiring the determination result.

For example, the light source control circuit 27 repeats the operation (determination) in steps S1, S3 and S5 in FIG. 7 unless the operation in step S2 in FIG. 7 is performed during a period from pressing of the scan start switch of the input device 11 to pressing of a scan end switch (not shown), for example. Furthermore, the light source control circuit 27 performs operations similar to the series of operations in FIG. 7 to thereby determine occurrence/non-occurrence of a failure in the LD drive circuit 23, occurrence/non-occurrence of deterioration of the LD 21B, and occurrence/non-occurrence of deterioration of the PD 25B and acquire the determination results, and controls the LD drive circuit 23 and/or the I/V conversion circuit 26B according to the acquired determination results. Furthermore, the light source control circuit 27 performs operations similar to the series of operations in FIG. 7 to thereby determine occurrence/non-occurrence of a failure in the LD drive circuit 23, occurrence/non-occurrence of deterioration of the LD 21C, and occurrence/non-occurrence of deterioration of the PD 25C and acquire the determination results, and controls the LD drive circuit 23 and/or the I/V conversion circuit 26C according to the acquired determination results.

As described above, according to the series of operations in FIG. 7, occurrence of deterioration of the LD 21A and/or the PD 25A and occurrence of a failure in the LD drive circuit 23 may be separately detected. Also, according to the series of operations in FIG. 7, for example, when a determination result that indicates occurrence of deterioration of the LD 21A is acquired, control of amplifying the drive current IDA is performed, and thus, the light source device 2 may be continued to be used in a state where reduction in the amount of emission of R light caused by the deterioration of the LD 21A is compensated. Moreover, according to the series of operations in FIG. 7, for example, when a determination result that indicates occurrence of deterioration of the PD 25A is acquired, control of increasing the conversion factor MPA is performed, and thus, the light source device 2 may be continued to be used in a state where reduction in the received amount of R light caused by the deterioration of the PD 25A is compensated. Therefore, according to the present embodiment, the period when the light source device 2 (and the endoscope system 1) can be continuously used may be increased than in the past.

Note that, according to the present embodiment, the operation in step S1 in FIG. 7 and the operation in step S3 in FIG. 7 may be switched, for example. That is, according to the present embodiment, the light source control circuit 27 may perform operations to determine occurrence/non-occurrence of a failure in the LD drive circuit 23 based on the detected amount that is obtained by detecting the magnitude of the forward voltage VFA and to acquire the determination result, and to determine occurrence/non-occurrence of deterioration of the LD 21A and/or the PD 25A based on the detected amount that is obtained by detecting the drive current IDA and the detected amount that is obtained by detecting the magnitude of the output current IPA and to acquire the determination result. Moreover, in the case where a determination result that indicates occurrence of deterioration of the LD 21A is obtained by such an operation, the light source control circuit 27 may control the LD drive circuit 23 so as to amplify the drive current IDA to the reference drive current IDT, for example.

Note that the present invention is not limited to the embodiment described above, and various modifications and applications may, of course, be made within the range of the gist of the invention.

What is claimed is:

1. A light source device comprising:
a light-emitting device configured to emit laser light;
a light-receiving device configured to receive a part of the laser light emitted from the light-emitting device, and to generate, and output, a received light signal having an output current of a magnitude according to an amount of the received laser light;
a drive signal supply section configured to generate, and supply to the light-emitting device, a drive signal for driving the light-emitting device; and
a determination section configured to determine occurrence/non-occurrence of a failure in the drive signal supply section based on a first detected amount that is obtained by detecting one of a magnitude of a drive current of the drive signal and a magnitude of a forward voltage of the light-emitting device and to acquire a determination result, and to determine occurrence/non-occurrence of deterioration of the light-emitting device and/or the light-receiving device based on a second detected amount that is obtained by detecting another of the magnitude of the drive current and the magnitude of the forward voltage and a third detected amount that is obtained by detecting a magnitude of the output current and to acquire a determination result.

2. The light source device according to claim 1, further comprising a light source control section configured to perform control so as to stop supply of the drive signal to the light-emitting device in a case where a determination result that indicates occurrence of a failure in the drive signal supply section is acquired by the determination section.

3. The light source device according to claim 2, wherein, in a case where a determination result that indicates non-occurrence of a failure in the drive signal supply section is acquired by the determination section, and a determination result that indicates occurrence of deterioration of the light-emitting device is acquired by the determination section, the light source control section performs control so as to increase the second detected amount.

4. The light source device according to claim 2, wherein, in a case where a determination result that indicates non-occurrence of a failure in the drive signal supply section is acquired by the determination section, and a determination result that indicates occurrence of deterioration of the light-receiving device is acquired by the determination section, the light source control section performs control so as to increase the third detected amount.

* * * * *